US012790647B2

(12) United States Patent
Lilley et al.

(10) Patent No.: US 12,790,647 B2
(45) Date of Patent: Nov. 10, 2026

(54) BIOMARKERS FOR THE DIAGNOSIS OF PARKINSON'S DISEASE

(71) Applicant: Neu Bio, Inc., Eugene, OR (US)

(72) Inventors: Patrick Lilley, Aliso Viejo, CA (US); Gwendelyn Lilley, Aliso Viejo, CA (US)

(73) Assignee: Neu Bio, Inc., Eugene, OR (US)

( * ) Notice: Subject to any disclaimer, the term of this patent is extended or adjusted under 35 U.S.C. 154(b) by 0 days.

(21) Appl. No.: 17/994,894

(22) Filed: Nov. 28, 2022

(65) Prior Publication Data

US 2023/0295727 A1 Sep. 21, 2023

Related U.S. Application Data

(60) Provisional application No. 63/321,651, filed on Mar. 18, 2022.

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2016/0244833 A1* 8/2016 Potashkin ............ C12Q 1/6883
2019/0049466 A1* 2/2019 Bolotina .............. C12Q 1/6883

OTHER PUBLICATIONS

Liu et al Clinical Immunology. 2004. 112: 225-230 (Year: 2004).*
Coleman, R. Drug Discovery Today. 2003. 8: 233-235 (Year: 2003).*
Min et al BMC Genomics. 2010. 11:96 (Year: 2010).*
Palmer et al. BMC Genomics. 2006. 7:115 (Year: 2006).*
Wegler et al NAR Genom Bioinform. Mar. 2020. 2(1): Iqz010, 11 pages (Year: 2020).*
Wang et al Molecular Medicine Reports. 2017. 16: 3769-3776 (Year: 2017).*
Scherzer et al PNAS. 2007. 104: 955-960 (Year: 2007).*
Jiang et al FEBS Open Bio. 2019. 9: 1460-1468 (Year: 2019).*
Chikina (Movement Disorders. 30(6): 813-821 and Supplementary Information, 25 pages total (Year: 2015).*
Chikina et al. Movement Disorders. 30(6): 813-821 and Supporting Data, 25 pages total (Year: 2015).*

* cited by examiner

*Primary Examiner* — Carla J Myers
(74) *Attorney, Agent, or Firm* — ENTRALTA PLLC; James Fleming; Peter Weinstein

(57) ABSTRACT

Embodiments of the invention include a system and method of using biomarkers in the diagnosis of Parkinson's disease. A subject can be screened for Parkinson's disease based on altered expression of one or more biomarkers in blood, plasma or saliva from the subject. Embodiments include 18 specific mRNA biomarkers to screen or distinguish healthy individuals from individuals affected with Parkinson's disease. Embodiments also include 33 specific protein biomarkers to screen or distinguish healthy individuals from individuals affected with Parkinson's disease. The biomarkers can also be used to determine the prognosis of a subject with the disease and identify early-onset and/or asymptomatic Parkinson's disease.

7 Claims, 3 Drawing Sheets

Detailed List of mRNA Biomarkers

| | Marker ID | Accession, Standard ID | Gene | Description |
|---|---|---|---|---|
| 1 | 204410_at | NM_004681, 9068 | EIF1AY | eukaryotic translation initiation factor 1A, Y-linked |
| 2 | 216677_at | U20648, 154 | ZNF154 | zinc finger protein 154 |
| 3 | 214889_at | AL080065, 25854 | FAM149A | family with sequence similarity 149 member A |
| 4 | 209840_s_at | AI221950, 54674 | LRRN3 | LLRN3, leucine rich repeat neuronal 3 |
| 5 | 220860_at | NM_013357, 29942 | PURG | purine rich element binding protein G |
| 6 | 203154_s_at | NM_005884, 10298 | PAK4 | PAK4, p21 (RAC1) activated kinase 4 |
| 7 | 204253_s_at | AA454701, NM_000376.1 | VDR | vitamin D (1,25- dihydroxyvitamin D3) receptor (VDR), transcript variant 1 |
| 8 | 214584_x_at | R99037, 32 | ACACB | ACACB (ACC2), acetyl-CoA carboxylase beta |
| 9 | 211663_x_at, 212187_x_at | M61900, 5730 NM_000954 | PTGDS | prostaglandin D2 synthase |
| 10 | 216676_x_at | AC006293, 115653 | KIR3DL3 | killer cell immunoglobulin like receptor, three Ig domains and long cytoplasmic tail 3 |
| 11 | 217885_at | NM_018085, 55705 | IPO9 | importin 9 |
| 12 | 221815_at | BE671816 | ABHD2 | abhydrolase domain containing 2 |
| 13 | 207237_at | NM_002232, 3738 | KCNA3 | potassium voltage-gated channel subfamily A member 3 |
| 14 | 204450_x_at | NM_000039, 335 | APOA1 | apolipoprotein A1 |
| 15 | 212262_at | AA149639, 9444 | QKI | QKI, QKI KH domain containing RNA binding |
| 16 | 221752_at | AL041728, 54434 | SSH1 | slingshot protein phosphatase 1 |
| 17 | 213146_at | AA521267, 23135 | KDM6B | lysine demethylase 6B |
| 18 | 200601_at | U48734 | ACTN4 | actinin alpha 4 |

FIG. 1

Detailed List of Protein Biomarkers

| | Marker ID | Standard ID | Gene | Description |
|---|---|---|---|---|
| 1 | 1227 | NM_152772.1 | TCP11L2 | T-complex protein 11-like protein 2 |
| 2 | 1091 | NM_021088.1 | ZNF2 | Zinc finger protein 2 |
| 3 | 9368 | NM_016507.1 | CDK12 | Cell division cycle 2-related protein kinase 7 |
| 4 | 9398 | BC013158.1 | APBB3 | amyloid beta (A4) precursor protein-binding, family B, member 3 (APBB3) |
| 5 | 8103 | NM_003437.2 | ZNF136 | zinc finger protein 136 (ZNF136) |
| 6 | 5725 | NM_002211.2 | ITGB1 | integrin, beta 1 (fibronectin receptor, beta polypeptide, antigen CD29 includes MDF2, MSK12) (ITGB1), transcript variant 1A |
| 7 | 1359 | NM_002488.2 | NDUFA2 | NADH dehydrogenase (ubiquinone) 1 alpha subcomplex, 2, 8kDa (NDUFA2) |
| 8 | 7227 | BC003604.1 | IPO9 | Importin-9 |
| 9 | 4810 | XM_378879.2 | LOC400763 | PREDICTED: Homo sapiens hypothetical LOC400763 (LOC400763) |
| 10 | 9094 | NM_012241.2 | SIRT5 | sirtuin (silent mating type information regulation 2 homolog) 5 (S. cerevisiae) (SIRT5), transcript variant 1 |
| 11 | 1422 | NM_020750.1 | XPO5 | exportin 5 (XPO5) |
| 12 | 8547 | NM_007360.1 | KLRK1 | killer cell lectin-like receptor subfamily K, member 1 (KLRK1) |
| 13 | 237 | BC007022.1 | SAA1 | serum amyloid A1 (SAA1) |
| 14 | 1568 | BC001632.1 | NDUFV2 | NADH dehydrogenase [ubiquinone] flavoprotein 2, mitochondrial |
| 15 | 4682 | PV4395 | MARK1 | Serine/threonine-protein kinase MARK1 |
| 16 | 7389 | NM_153339.1 | PUSL1 | pseudouridylate synthase-like 1 (PUSL1) |
| 17 | 1019 | BC005378.1 | C4BPB | complement component 4 binding protein, beta (C4BPB) |
| 18 | 831 | BC006105.1 | C6orf134 | chromosome 6 open reading frame 134 (C6orf134) |
| 19 | 5075 | PHC0205 | IL20 | interleukin 20 (IL20) |
| 20 | 5076 | PHC1244 | CCL19 | chemokine (C-C motif) ligand 19 (CCL19) |

FIG. 2

| | Marker ID | Standard ID | Gene | Description |
|---|---|---|---|---|
| 21 | 275 | BC014441.1 | NSUN4 | NOL1/NOP2/Sun domain family, member 4 (NSUN4) |
| 22 | 6710 | NM_022438.1 | MAL | Myelin and lymphocyte protein |
| 23 | 227 | BC013966.2 | FAM64A | family with sequence similarity 64, member A (FAM64A) |
| 24 | 7463 | BC017305.1 | SIRT7 | sirtuin (silent mating type information regulation 2 homolog) 7 (S. cerevisiae) (SIRT7) |
| 25 | 7314 | BC053557.1 | ZNF740 | zinc finger protein 740 (ZNF740) |
| 26 | 211 | NM_006555.2 | YKT6 | YKT6 v-SNARE homolog (S. cerevisiae) (YKT6) |
| 27 | 2376 | NM_145810.1 | CDCA7 | cell division cycle associated 7 (CDCA7), transcript variant 2 |
| 28 | 6324 | BC012499.1 | SIRT1 | NAD-dependent deacetylase sirtuin-1 |
| 29 | 690 | NM_004549.2 | NDUFC2 | NADH dehydrogenase (ubiquinone) 1, subcomplex unknown, 2, 14.5kDa (NDUFC2) |
| 30 | 2990 | BC041174.1 | CYP2B7P1 | cytochrome P450, family 2, subfamily B, polypeptide 7 pseudogene 1 (CYP2B7P1) |
| 31 | 365 | BC006558.2 | HCFC2 | Host cell factor 2 |
| 32 | 4052 | BC030814.1 | IGKV1-5 | immunoglobulin kappa variable 1-5 (IGKV1-5) |
| 33 | 985 | NM_003041.1 | SLC5A2 | Sodium/glucose cotransporter 2 |

FIG. 2 (cont.)

BIOMARKERS FOR THE DIAGNOSIS OF PARKINSON'S DISEASE

CROSS REFERENCE TO RELATED APPLICATIONS

The present application is claims priority to US provisional patent application No. 63/321,651 filed Mar. 18, 2022 which is incorporated by reference.

FIELD OF THE INVENTION

The invention relates to the diagnosis of disease using biomarkers, and more specifically, to a system and method of diagnosing Parkinson's disease based on altered expression of one or more specific mRNAs or proteins.

BACKGROUND

Parkinson's disease (PD) is a long-term degenerative disorder of the central nervous system that mainly affects the motor system. PD is the second most common neurodegenerative disease in adults, with an average life span of ten years from the diagnosis. The symptoms usually emerge slowly, and as the disease worsens, non-motor symptoms become more common. The most obvious early symptoms are tremor, rigidity, slowness of movement, and difficulty with walking. Cognitive and behavioral problems may also occur with depression, anxiety, and apathy. Parkinson's disease dementia becomes common in the advanced stages of the disease. Those with Parkinson's can also have problems with their sleep and sensory systems. The motor symptoms of the disease result from the death of cells in the substantia nigra, a region of the midbrain, leading to a dopamine deficit. The cause of this cell death is not well understood but involves the build-up of misfolded proteins into Lewy bodies in the neurons. Collectively, the main motor symptoms are also known as parkinsonism or a parkinsonian syndrome.

The cause of PD is unknown, with both inherited and environmental factors believed to play a role. Those with an affected family member are at an increased risk of getting the disease with certain genes known to be inheritable risk factors. Other risk factors include exposure to certain pesticides and a history of head injuries. Diagnosis of PD is based mainly on symptoms with motor symptoms usually being the chief complaint. Tests such as neuroimaging (i.e., magnetic resonance imaging or imaging to look at dopamine neuronal dysfunction known as DaT scan) can be used to help rule out other diseases. PD typically occurs in people over the age of 60, of whom about one percent are affected. Males are more often affected than females. Early-onset PD refers to the onset of the disease in people younger than 50 years old. PD affects about 10 M people worldwide and its incidence continues to grow as populations age. The prevalence of PD is expected to increase 30% from in the U.S. by the year 2030 at an annual cost of $52 billion.

Despite decades of research and billions of dollars, much about PD remains unknown. There is presently no simple or accurate test for PD. Moreover, there is no method of early detection. Diagnosing PD is subjective as a physician initially assesses for PD with a medical history and neurological examination. Focus is put on confirming motor symptoms (e.g., bradykinesia, rest tremor, etc.) and supporting tests with clinical diagnostic criteria. The only objective definitive diagnostic test requires tissue examination which is usually delayed until autopsy. Moreover, the clinical course of the illness over time may reveal an illness is not PD, requiring that the clinical presentation be periodically reviewed to confirm the accuracy of the diagnosis.

Multiple causes can lead to diseases that present similar symptoms that are similar to PD. Parkinsonism refers to symptoms of Parkinson's disease (e.g., slow movements and tremors) that are caused by another condition. Stroke, certain medications, and toxins can cause "secondary parkinsonism" and need to be assessed during visit. Parkinson-plus syndromes, such as progressive supranuclear palsy and multiple system atrophy, must also be considered and ruled out due to different treatment and disease progression. Faster progression rates, early cognitive dysfunction or postural instability, minimal tremor, or symmetry at onset may indicate a Parkinson-plus disease rather than PD itself.

There is no cure for PD. Rather, treatment aims to reduce the effects of the symptoms. Initial treatment is typically with the medications levodopa (L-DOPA), MAO-B inhibitors, or dopamine agonists. As the disease progresses, these medications generally become less effective. Moreover, involuntary muscle movements become more frequent and intense. Diet and certain forms of rehabilitation have shown some effectiveness at improving symptoms. Surgery to place microelectrodes for deep brain stimulation has been used to reduce motor symptoms in severe cases.

Because of the limitations of accurately detecting PD, it is difficult to detect in its early stages when therapies can be most effective. It is also difficult to study disease progression and develop drugs/therapies. Further, it is difficult for drug developers to properly recruit patients for their clinical trials. Accordingly, there is a need for accurate and affordable noninvasive methods of diagnosing PD.

Biomarkers are a non-invasive and cost-effective means to aid in clinical management of patients, particularly in areas of disease detection, prognosis, monitoring and therapeutic stratification. For a serological biomarker to be useful for early detection, its presence in serum must be relatively low in healthy individuals and those with benign disease. The biomarker should preferably be tissue specific, such that a change in serum level can be directly attributed to disease (e.g., PD) of that tissue.

For example, serum PSA is commonly used for prostate cancer screening in men over 50, but its usage remains controversial due to serum elevation in benign disease as well as prostate cancer. Nevertheless, PSA represents one of the most useful serological markers currently available. PSA is strongly expressed in only the prostate tissue of healthy men, with low levels in serum established by normal diffusion through various anatomical barriers. These anatomical barriers are disrupted upon development of prostate cancer, allowing increased amounts of PSA to enter circulation. Other common serological biomarkers include carcinoembryonic antigen (CEA) and carbohydrate antigen 19.9 (CA19.9) for gastrointestinal cancer, CEA, CYFRA 21-1 (cytokeratin 19 fragment), neuron-specific enolase (NSE), tissue polypeptide antigen (TPA), progastrin-releasing peptide (pro-GRP), and SCC antigen for lung cancer, CA 125 for ovarian cancer and prostate-specific antigen (PSA, also known as KLK3) in prostate cancer.

There is a need for improved diagnostic assays and methods of detecting PD. Conventional methods of diagnosing PD are subjective and can be unreliable. Moreover, there is no method of prognosing PD or monitoring its progression other than observing its symptoms. Thus, there is a need for the identification of alternative molecular markers that overcome these limitations. Embodiments of the invention include methods of detecting and prognosing PD using mRNA and protein biomarkers.

SUMMARY OF THE INVENTION

The following summary is provided to facilitate an understanding of some of the innovative features unique to the disclosed embodiments and is not intended to be a full description. A full appreciation of the various aspects of the embodiments disclosed herein can be gained by taking into consideration the entire specification, claims and abstract as a whole.

The methods and assays disclosed herein are directed to the examination of the amount of one or more biomarkers in a biological sample, wherein the determination of that amount is predictive or indicative of the presence and/or severity of Parkinson's disease (PD). For example, the methods and assays can detect asymptomatic PD and distinguish between Stage I-Stage V PD. The disclosed methods and assays provide for convenient, efficient, and potentially cost-effective means to obtain data and information useful in assessing appropriate or effective therapies for treating patients.

Accordingly, the biomarkers and methods described herein can be used for 1) diagnosis of PD (i.e., determining presence or absence of a condition), 2) determining severity (i.e., determining state, stage, etc.), 3) prognosis (i.e., predicting progression with or without treatment), or 4) prediction of PD (i.e., likelihood of getting the disease in the future, or predicting yes/no that the person will get it within a specific time-frame).

Methods for detecting biomarkers to be assessed include protocols that examine the presence and/or expression of a desired nucleic acid. Tissue or cell samples from mammals can be conveniently assayed for, e.g., genetic-marker mRNAs or DNAs using Northern, dot-blot, or polymerase chain reaction (PCR) analysis, array hybridization, RNase protection assay, or using DNA SNP chip microarrays, which are commercially available, including DNA microarray snapshots. For example, real-time PCR (RT-PCR) assays such as quantitative PCR assays are well known in the art. Methods also include assays to detect/quantify specific proteins such as immune-affinity assays (e.g., ELISA, Western blot, flow cytometry, etc.).

More specifically, embodiments include methods of detecting PD based on specific mRNAs and proteins that have altered expression levels. The Applicant has identified 18 mRNAs and 33 proteins that can be used as biomarkers to distinguish healthy individuals from individuals affected with PD. The use of biomarkers is non-invasive and potentially more sensitive than conventional methods. The biomarkers can distinguish between PD from secondary parkinsonism and Parkinson-plus syndromes. The biomarkers can also detect early-onset or asymptomatic PD. Embodiments also include methods of prognosis, patient monitoring and distinguishing between PD and ailments that present signs/symptoms similar to PD (e.g., Parkinson-plus syndromes).

In one embodiment, the method includes one or more mRNA biomarkers. In one embodiment, the method includes one or more protein biomarkers. In one embodiment, the method includes a combination of one or more mRNA biomarkers and one or more protein biomarkers.

Embodiments include the use of one or more of the following genes (or mRNAs) as biomarkers: VDR, PTGDS, KCNA3 (Kv1.3), PAK4, P21 (RAC1), KDM6B (JMJD3), APOA1, LRRN3, QKI, ACACB (ACC2), ACTN4, SSH1, KIR3DL3, ZNF154, EIF1AY, IPO9, ABHD2, PURG and FAM149A.

Embodiments include the use of one or more of the following proteins as biomarkers: C4BPB, SIRT7, SIRT1, SIRT5, YKT6, NDUFV2, IL20, KLRK1 (NKG2D or CD314), NDUFA2, NDUFC2, SLC5A2 (SGLT2), ZNF2, MAL, MARK1, SAA1, ITGB1, NSUN4, CDK12, CCL19 (ELC), XPO5, APBB3, ZNF740, C6orf134 (ATAT1), CDCA7, TCP11L2, IGKV1-5, HCFC2, FAM64A (PIMREG), PUSL1, CYP2B7P1, LOC400763, ZNF136 and IPO9.

Embodiments also include the use of the mRNAs and proteins identified herein as therapeutic targets for treating PD.

Embodiments include a method of detecting PD or determining a prognosis of a subject with PD, that includes steps of a) measuring the expression level of at least one mRNA in a test sample of the subject; b) comparing the expression level of the mRNA in the test sample to a level in a base sample; and c) detecting or determining the prognosis of PD based on altered expression the mRNA in the test sample. The method can be used with blood, serum other bodily fluids including saliva. In other embodiments, the method compares levels of at least one protein between the base sample and the test sample. The method can also determine progression of PD by distinguishing between, for example, the five stages of PD.

Embodiments also include a method of detecting PD or determining a prognosis of a test subject with PD, that includes steps of: a) measuring expression levels of two or more mRNAs in samples from subjects with PD; b) measuring expression levels of the same mRNAs in samples from healthy subjects; c) comparing the expression levels of the mRNAs in the samples from the subjects with PD to the levels in the samples from the healthy subjects; d) identifying mRNAs that have altered levels of expression in the samples from the subjects with PD; e) creating a biomarker fingerprint from the mRNAs with altered levels of expression; and f) diagnosing or determining the prognosis of PD in the test subject by comparing of levels of mRNAs from the test subject to those in the biomarker fingerprint. In other embodiments, the method compares levels of two or more proteins between healthy subjects and subjects with PD to create the biomarker fingerprint.

In aspects, the methods described herein include a treatment step. Treatment can include administering a therapeutic amount of a dopamine agonist to a patient with PD.

Embodiments also include a diagnostic kit for diagnosing PD or determining a prognosis of a subject with PD. The kit can include a plurality of nucleic acid molecules, each nucleic acid molecule encoding a mRNA sequence. The nucleic acid molecules identify variations in expression levels of one or more mRNAs in a plasma or saliva sample from a test subject. The expression levels of one or more mRNAs can represent a nucleic acid expression fingerprint that is indicative for the presence of a PD. In other embodiments, the kit utilizes an immune-affinity based assay to compare levels of protein to diagnose PD or determine a prognosis of a subject with PD.

BRIEF DESCRIPTION OF THE FIGURES

The accompanying drawings illustrate aspects of the present invention. In such drawings:

FIG. 1 is a detailed list of mRNA biomarkers for detection and/or prognosis of Parkinson's disease (PD).

FIG. 2 is a detailed list of protein biomarkers for detection and/or prognosis of Parkinson's disease (PD).

DEFINITIONS

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As applicable, the terms "about" or "generally", as used herein in the specification and appended claims, and unless otherwise indicated, means a margin of ±20%. Also, as applicable, the term "substantially" as used herein in the specification and appended claims, unless otherwise indicated, means a margin of ±10%. It is to be appreciated that not all uses of the above terms are quantifiable such that the referenced ranges can be applied.

The term "algorithm" refers to a specific set of instructions or a definite list of well-defined instructions for carrying out a procedure, typically proceeding through a well-defined series of successive states, and eventually terminating in an end-state.

The term "biomarker" refers generally to a DNA, RNA, protein, carbohydrate, or glycolipid-based molecular marker, the expression or presence of which in a subject's sample can be detected by standard methods (or methods disclosed herein) and is predictive or prognostic of the effective responsiveness or sensitivity of a mammalian subject with PD. Biomarkers may be present in a test sample but absent in a control sample, absent in a test sample but present in a control sample, or the amount of biomarker can differ between a test sample and a control sample. For example, genetic biomarkers assessed (e.g., specific mutations and/or SNPs) can be present in such a sample, but not in a control sample, or certain biomarkers are seropositive in the sample, but seronegative in a control sample. Also, optionally, expression of such a biomarker may be determined to be higher than that observed for a control sample. The terms "marker" and "biomarker" are used herein interchangeably.

The term "altered expression" or "differential level" of a biomarker may include either an increased or decreased level. For example, an altered expression level can refer to a biomarker level that is decreased by at least 5%, at least 10%, at least 20%, at least 30%, at least 40%, at least 50%, at least 60%, at least 70%, at least 80%, at least 90% or at least 100% (i.e., indicative of the absence of the biomarker molecule). In another embodiment, an altered expression level refers to a level that is increased by at least 5%, at least 10%, at least 20%, at least 30%, at least 40%, at least 51%, at least 60%, at least 70%, at least 80%, at least 90%, at least 100%, at least 110%, at least 120%, at least 130%, at least 140%, at least 150%, at least 200% or more.

The term "Secondary parkinsonism" refers to a condition in which symptoms similar to Parkinson's disease are caused by certain medicines, a different nervous system disorder or another illness. Parkinson's disease is caused mainly by the degeneration of nerve cells in the brain, while the causes of parkinsonism are numerous, ranging from the side effects of medications to chronic head traumas to metabolic diseases to toxins to neurological diseases. Parkinsonism also refers to any condition that involves the types of movement problems seen in Parkinson's disease.

The term "Parkinson's plus syndromes" or "atypical Parkinson's" refers to a group of conditions that have similar symptoms to Parkinson's disease but are not Parkinson's. There are four main types: Progressive Supranuclear Palsy (PSP), Dementia With Lewy Bodies, Multiple System Atrophy and Corticobasal Degeneration.

The term "Lewy body" refers to a distinctive neuronal inclusion that is found in the substantia nigra and other specific brain regions in Parkinson's disease. Lewy bodies are abnormal aggregations of protein that develop inside nerve cells affected by Parkinson's disease. Lewy bodies appear as spherical masses in the cytoplasm that displace other cell components.

As used herein, "additional biomedical information" refers to one or more evaluations of an individual, other than using any of the biomarkers described herein, that are associated with PD risk. "Additional biomedical information" includes any of the following: physical descriptors of an individual, the height and/or weight of an individual, the gender of an individual, the ethnicity of an individual, smoking history, occupational history, exposure to known toxins/carcinogens (e.g., exposure to pesticides), family history of PD. Additional biomedical information can be obtained from an individual using routine techniques known in the art, such as from the individual themselves by use of a routine patient questionnaire or health history questionnaire, etc., or from a medical practitioner, etc. Alternately, additional biomedical information can be obtained from routine imaging techniques, including CT imaging (e.g., low-dose CT imaging) and X-ray. Testing of biomarker levels in combination with an evaluation of any additional biomedical information may, for example, improve sensitivity, specificity, and/or AUC for detecting PD as compared to biomarker testing alone or evaluating any particular item of additional biomedical information alone.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., PD samples and normal or control samples). ROC curves are useful for plotting the performance of a particular feature (e.g., any of the biomarkers described herein and/or any item of additional biomedical information) in distinguishing between two populations (e.g., cases having PD and controls without PD). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

As used herein, "detecting" or "determining" with respect to a biomarker value includes the use of both the instrument required to observe and record a signal corresponding to a biomarker value and the material/s required to generate that signal. In various embodiments, the biomarker value is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

The term "prognosis" refers to the forecast or likely outcome of a disease. As used herein, it refers to the probable outcome of PD, including whether the disease will respond to treatment or mitigation efforts and/or the likelihood that the disease will progress. The stage of PD can be considered in determining a prognosis of a subject.

The term "stage" or "stage of Parkinson's disease" refers to one of the following five stages. Stage I is characterized by mild symptoms that do not interfere with one's daily activities. Such symptoms can include, for example, movement symptoms (e.g., tremors, rigidity, and bradykinesia) affecting one side of the body (i.e., unilateral), mild problems with posture and balance, slight difficulty walking and mild changes in facial expressions. Stage II is characterized by these symptoms becoming worse and making daily activities more difficult. However, subjects are generally able to look after themselves. Symptoms can include sporadic movements (e.g., tremors, rigidity, and bradykinesia) that affect both sides of the body (bilateral), difficulty walking, difficulty balancing, poor posture and reduced facial expressions. In Stage III, symptoms are more severe than those of stage II. However, the person is still independent. Loss of balance and bradykinesia (slowness of movements) are the hallmark symptoms of this stage. Daily activities such as eating, bathing and dressing are significantly impaired. In Stage IV, independent living is almost impossible due to limitations in daily activities such as eating, bathing, dressing, sleeping and walking. The person may be able to stand on their own but need assistance for moving around. Stage V is characterized by severe symptoms and standing on one's own may be impossible. The person generally becomes bedridden and requires a wheelchair to be moved around. All daily activities are impaired, requiring a full-time caregiver. Symptoms can include delusions, hallucinations, loss of smell, constipation, poor reasoning and memory, weight loss, sleep disturbances and vision problems.

The term "fingerprint," "disease fingerprint," or "biomarker signature" refers to a plurality or pattern of biomarkers that have elevated or reduced levels in a subject with disease. A fingerprint can be generated by comparing subjects with the disease to healthy subjects and used for screening/diagnosis of the disease.

The term "miRNA" or "micro RNA," "miRNA biomarkers," or "MicroRNAs" refers to small endogenous RNA molecules that can be used as serum diagnostic biomarkers for diseases including PD.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "medicament" refers to an active drug to treat PD, or the signs or symptoms or side effects of PD.

The term "plasma" or "blood plasma" refers to the liquid portion of the blood that carries cells and proteins throughout the body. Plasma can be separated from the blood by spinning a tube of fresh blood containing an anticoagulant in a centrifuge until the blood cells fall to the bottom of the tube.

The term "PCR" or "polymerase chain reaction" refers to a common method used to make many copies of a specific DNA segment. Variations of the technique can be used to determine the presence and amount of one or more mRNAs in a sample. For example, a hydrolysis probe-based stem-loop quantitative reverse-transcription PCR (RT-qPCR) assay can be conducted to confirm and/or quantify the concentrations of selected mRNAs in serum samples from patients and controls.

The term "sample" refers to a biological sample obtained from an individual, body fluid, or body tissue. Body fluids are, for example, lymph, sera, whole fresh blood, peripheral blood mononuclear cells, frozen whole blood, plasma (including fresh or frozen), urine, saliva, semen, synovial fluid and spinal fluid. Samples also include synovial tissue, skin, hair follicle, and bone marrow. Methods for obtaining tissue biopsies and body fluids from mammals are well known in the art.

The term "subject" or "patient" refers to a human patient.

An mRNA that is "upregulated" generally refers to an increase in the level of expression of the mRNA in response to a given treatment or condition. An mRNA that is "downregulated" generally refers to a "decrease" in the level of expression of the mRNA in response to a given treatment or condition. In some situations, the mRNA level can remain unchanged upon a given treatment or condition. An mRNA from a patient sample can be "upregulated," i.e., the level of mRNA can be increased, for example, by about 5%, about 10%, about 20%, about 30%, about 40%, about 50%, about 60%, about 70%, about 90%, about 100%, about 200%, about 300%, about 500%, about 1,000%, about 5,000% or more of the comparative control mRNA level or a reference level. Alternatively, an mRNA can be "downregulated," i.e., the level of mRNA level can be decreased, for example, by about 99%, about 95%, about 90%, about 80%, about 70%, about 60%, about 50%, about 40%, about 30%, about 20%, about 10%, about 5%, about 2%, about 1% or less of the comparative control mRNA level or a reference level.

Similarly, the level of a polypeptide, protein, or peptide from a patient sample can be increased as compared to a control or a reference level. This increase can be about 5%, about 10%, about 20%, about 30%, about 40%, about 50%, about 60%, about 70%, about 90%, about 100%, about 200%, about 300%, about 500%, about 1,000%, about 5,000% or more of the comparative control protein level or a reference level. Alternatively, the level of a protein biomarker can be decreased. This decrease can be, for example, present at a level of about 99%, about 95%, about 90%, about 80%, about 70%, about 60%, about 50%, about 40%, about 30%, about 20%, about 10%, about 5%, about 2%, about 1% or less of the comparative control protein level or a reference level.

The term "nucleic acid probe" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "standard ID" refers to a standardized identification for genes provided by the Human Gene Nomenclature Committee (HGNC). The term "accession" or "accession ID" refers to a unique identifier for a sequence record in a database such as GenBank. An accession number applies to the complete record and is usually a combination of a letters and numbers, such as a single letter followed by five digits (e.g., U12345) or two letters followed by six digits (e.g., AF123456).

The term "marker ID," "probe set identifier," or "Affymetrix probe set ID" refers to the identifier that refers to a set of probe pairs selected to represent expressed sequences on an array. (at =all the probes hit one known transcript; _a=all probes in the set hit alternate transcripts from the same gene; _s=all probes in the set hit transcripts from different genes; _x=some probes hit transcripts from different genes).

Other technical terms used herein have their ordinary meaning in the art that they are used, as exemplified by a variety of technical dictionaries. The particular values and configurations discussed in these non-limiting examples can be varied and are cited merely to illustrate at least one embodiment and are not intended to limit the scope thereof.

DETAILED DESCRIPTION

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

Recent studies have demonstrated the presence of mRNAs/proteins in saliva and circulating blood and their potential for use as biomarkers in the diagnosis of various diseases. Applicants present the use as specific biomarkers for early detection of Parkinson's disease (PD).

The Applicant has recognized mRNA and protein expression profiling in subjects with PD. Specific mRNAs and proteins or "biomarkers" are aberrantly expressed in tissues affected by PD as compared to healthy tissue. Moreover, biomarker expression can provide insights into cellular processes involved in the progression of PD. Thus, mRNA expression levels can also be used for prognosis. Specifically, the technology provides diagnostic methods for predicting and/or prognosticating the effectiveness of treatment.

The present invention is based on the finding that PD can be reliably identified based on particular biomarker expression profiles with high sensitivity and specificity. The expression of biomarkers typically includes both up- and down-regulated levels of mRNAs/proteins. An analysis of mRNA/protein expression biomarkers allows for creation of a "fingerprint" by analyzing mRNA/protein expression patterns in diseased and healthy subjects. Thereafter, individual mRNA/protein expression levels can be used for the detection of PD at early stages of the disease (e.g., when asymptomatic). It is also possible to monitor progression of PD (e.g., between early, moderate and late stages) and distinguish PD from diseases that present similar signs/symptoms such as Parkinson-plus syndromes.

Early detection of PD is important for effective treatment. Medications and treatments can be more effective if they begin in early stages of PD, before progression of signs/symptoms. Further, the biomarkers can be used as therapeutic targets and to identify pathways for study of the disease.

Accordingly, embodiments include diagnostic markers or a molecular fingerprint, for quick and reliable identification and/or treatment of cells exhibiting or having a predisposition to develop PD. Embodiments further include methods of diagnosing PD based on specific mRNAs that have altered expression levels. While individual mRNAs can be monitored, the invention includes 18 mRNAs of particular value as biomarkers to screen or distinguish healthy individuals from individuals affected with disease. The mRNAs of particular interest (as detailed in Table 1 and FIG. 1) include: VDR, PTGDS, KCNA3 (Kv1.3), PAK4, P21 (RAC1), KDM6B (JMJD3), APOA1, LRRN3, QKI, ACACB (ACC2), ACTN4, SSH1, KIR3DL3, ZNF154, EIF1AY, IPO9, ABHD2, PURG and FAM149A.

Embodiments further include methods of diagnosing PD based on specific proteins that have altered expression levels. While individual proteins can be monitored, the invention includes 33 proteins of particular value as biomarkers to screen or distinguish healthy individuals from individuals affected with disease. The proteins of particular interest (as detailed in Table 2 and FIG. 2) include: C4BPB, SIRT7, SIRT1, SIRT5, YKT6, NDUFV2, IL20, KLRK1 (NKG2D or CD314), NDUFA2, NDUFC2, SLC5A2 (SGLT2), ZNF2, MAL, MARK1, SAA1, ITGB1, NSUN4, CDK12, CCL19 (ELC), XPO5, APBB3, ZNF740, C6orf134 (ATAT1), CDCA7, TCP11L2, IGKV1-5, HCFC2, FAM64A (PIMREG), PUSL1, CYP2B7P1, LOC400763, ZNF136 and IPO9.

The methods and materials can be used for assessing subjects (e.g., human patients) for PD. Specifically, the levels of markers can be used for 1) diagnosis (i.e., determining presence or absence of a condition), 2) determining severity (i.e., state or stage of PD), 3) prognosis (i.e., prediction of progression with or without treatment, including specific types of treatment), or 4) prediction (i.e., likelihood of getting the disease in the future, or predicting that a subject will get it within a specific period of time). For example, embodiments include materials and methods for using identifiable markers to assist clinicians in assessing PD disease activity, assessing the likelihood of response and outcomes of therapy, and predicting long-term disease outcomes. Further, subjects with PD can be diagnosed based on the presence of certain diagnostic indicators in plasma or saliva from the subject. Thus, the technology allows for the diagnosis of PD based on one or more combinations of markers.

Multiple mRNA and/or protein biomarkers can be used from a single serum or saliva sample taken from a subject. According to some embodiments, multiple biomarkers are assessed and measured from different samples taken from the patient. According to some embodiments, the subject technology is used for a kit for predicting, diagnosing or monitoring responsiveness of a PD treatment or therapy, wherein the kit is calibrated to measure marker levels in a sample from the patient.

According to some embodiments, the amount of biomarkers can be determined by using, for example, a reagent that specifically binds with the biomarker protein or a fragment thereof, (e.g., an antibody, a fragment of an antibody, or an antibody derivative). The level of expression can be determined using a method common in the art such as proteomics, flow cytometry, immunocytochemistry, immunohistochemistry, enzyme-linked immunosorbent assay, multichannel enzyme linked immunosorbent assay, and variations thereof. The expression level of a biomarker in the biological sample can also be determined by detecting the level of expression of a transcribed biomarker polynucleotide or fragment thereof encoded by a biomarker gene, which may be cDNA, mRNA or heterogeneous nuclear RNA (hnRNA). The step of detecting can include amplifying the transcribed biomarker polynucleotide and can use the method of quantitative reverse transcriptase polymerase chain reaction (rtPCR). The expression level of a biomarker can be assessed by detecting the presence of the transcribed biomarker polynucleotide or a fragment thereof in a sample with a probe which anneals with the transcribed biomarker polynucleotide or fragment thereof under stringent hybridization conditions.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits contain one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. Therefore, certain embodiments employ processes involving data stored in or transferred through one or more computer systems or other processing systems. Embodiments disclosed herein also relate to apparatus for performing these operations. This apparatus may be specially constructed for the required purposes, or it can be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel.

In some embodiments, a microprocessor is part of a system for determining the presence of one or more mRNA or proteins associated with a PD; generating standard curves; determining a specificity and/or sensitivity of an assay or marker; calculating an ROC curve; sequence analysis; all as described herein or is known in the art.

In some embodiments, a microprocessor is part of a system for determining the amount, such as concentration, of one or more mRNAs or proteins associated with PD; generating standard curves; determining a specificity and/or sensitivity of an assay or marker; calculating an ROC curve; sequence analysis; all as described herein or is known in the art. The amount of one or more mRNAs or proteins can be determined by abundance, measured per mole or millimole. The amount of mRNAs or proteins can be determined by fluorescence, other measurement using an optical signal or other measurement known to one of skill in the art.

In some embodiments, a microprocessor or computer uses an algorithm to measure the amount of an mRNA or multiple mRNAs (or proteins). The algorithm can include a mathematical interaction between two or more biomarkers or a mathematical transform of a marker measurement. The mathematical interaction and/or mathematical transform can be presented in a linear, nonlinear, discontinuous or discrete manner.

In some embodiments, a software or hardware component receives the results of multiple assays and determines a single value result to report to a user that indicates a PD risk based on the results of the multiple assays. Related embodiments can calculate a risk factor based on a mathematical combination (e.g., a weighted combination, a linear combination) of the results from multiple assays as disclosed herein.

Some embodiments include a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, memory stick, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media can include an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

In some embodiments, the disclosure provides a system for predicting progression of PD. The disease can be asymptomatic, early-stage, mid-stage or late-stage PD. In an embodiment, PD can be identified in an individual using a system that includes: an apparatus configured to determine expression levels of nucleic acids, proteins, peptides or other molecule from a biological sample taken from the individual; and hardware logic designed or configured to perform operations including: (a) receiving expression levels of a collection of signature genes/proteins/peptides from a biological sample taken from said individual, wherein the collection of signature genes/proteins/peptides includes at least one mRNA from those listed in Table 1 and/or at least one protein from those listed in Table 2.

Information relevant to the patient's diagnosis include, but are not limited to, age, ethnicity, medical history, family history, physical exam findings, neurological exam findings, imaging and lab tests, etc. These clinical variables may be included in the predictive model in various embodiments.

Once a biomarker or biomarker panel is selected, the biomarker or biomarker panel can be used in a method for diagnosing PD in an individual. In an embodiment, a biomarker or biomarker panel is selected, a method for diagnosing an individual that may be suffering from PD and can include one or more of the following steps: 1) collect or otherwise obtain a biological sample; 2) perform an analytical method to detect and measure the biomarker or biomarkers in the panel in the biological sample; 3) perform any data normalization or standardization required for the method used to collect biomarker values; 4) calculate a biomarker score; 5) combine the biomarker scores to obtain a total diagnostic score; and 6) report the individual's diagnostic score. This method of diagnosis can be conducted using a computer and software programs for analysis of data collected from nucleic acid, protein, peptide or other biological molecules. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

For both DNA and RNA, the nucleic acid can be isolated from a saliva, plasma, blood sample or cell biopsy. The DNA or RNA can be extracellular or extracted from a cell in the plasma or blood sample. For a protein or peptide or other biological molecule, such can be isolated from a saliva, plasma, blood sample or cell biopsy. The protein or peptide or other biological molecule can be extracellular or extracted from a cell in the saliva, plasma or a blood sample.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

The PD biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the biomarkers. The computer program may comprise multiple modules performing various functions or operations, such as a processing module for processing raw data and generating supplemental data and an analysis module for analyzing raw data and supplemental data to generate PD status and/or diagnosis. Diagnosing the status of PD can include generating or collecting any other information, including additional biomedical information, regarding the condition of the individual relative to the disease, identifying whether further tests may be desirable, or otherwise evaluating the health status of the individual.

The PD biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the PD biomarkers. The computer program can include multiple modules performing various functions or operations, such as a processing module for processing raw data and generating supplemental data and an analysis module for analyzing raw data and supplemental data to generate a PD status and/or diagnosis. Diagnosing PD status can include generating or collecting any other information, including additional biomedical information, regarding the condition of the individual relative to the disease, identifying whether further tests may be desirable, or otherwise evaluating the health status of the individual.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one embodiment, a computer program product is provided for indicating a likelihood of PD. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 1/Table 2; and code that executes a classification method that indicates a PD status of the individual as a function of the biomarker values.

In yet another embodiment, a computer program product is provided for indicating a likelihood of PD. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 1/Table 2; and code that executes a classification method that indicates a PD status of the individual as a function of the biomarker value.

The kit (i.e., diagnostic kit) can include reagents for determining, from a plasma (or other sample) of a subject, levels of mRNA and/or protein biomarkers based on assaying the nucleic acids, proteins, peptides or other biological molecule present in a sample. The nucleic acid can be a deoxyribonucleic acid (DNA), a ribonucleic acid (RNA) and/or an artificial nucleic acid, including an artificial nucleic acid analogue. Along with mRNAs, other RNAs include non-coding RNA (ncRNA), transfer RNA (tRNA), messenger RNA (mRNA), small interfering RNA (siRNA), piwi RNA (piRNA), small nucleolar RNA (snoRNA), small nuclear RNA (snRNA), extracellular RNA (exRNA), and ribosomal RNA (rRNA).

The disclosed methods and assays provide for convenient, efficient, and potentially cost-effective means to obtain data and information useful in assessing appropriate or effective therapies for treating patients. The kit can use conventional methods for detecting the biomarkers, whether a protein, peptide, other biological molecule or an RNA or a DNA to be assessed include protocols that examine the presence and/or expression of a desired nucleic acid in a sample. Tissue or cell samples from mammals can be conveniently assayed for, e.g., genetic-marker RNA, including in an embodiment an mRNA or DNAs using Northern, dot-blot, or polymerase chain reaction (PCR) analysis, array hybridization, RNase protection assay, or using DNA SNP chip microarrays, which are commercially available, including DNA micro array snapshots. For example, real-time PCR (RT-PCR) assays such as quantitative PCR assays are well known in the art.

Probes used for PCR can be labeled with a detectable marker, such as, for example, a radioisotope, fluorescent compound, bioluminescent compound, a chemiluminescent compound, metal chelator, or enzyme. Such probes and primers can be used to detect the presence of a mutation in a DNA, an RNA and in one embodiment, an mRNA in a sample and as a means for detecting a cell expressing the mRNA. As will be understood by the skilled artisan, a great many different primers and probes can be prepared based on known sequences and used effectively to amplify, clone, and/or determine the presence and/or levels of mRNAs.

Other methods include protocols that examine or detect a mutation in a DNA or an RNA. These other methods include protocols that examine or detect mRNAs in a tissue or cell sample by microarray technologies. Using nucleic acid microarrays, test and control RNAs, including in an embodiment, mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states can be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment.

The biomarkers of the present invention are particularly useful in PD diagnosis as their expression patterns are different when comparing healthy subjects with subjects that have PD. The expression of biomarkers typically includes both up- and down-regulated levels of mRNAs. In an embodiment, the biomarkers set forth herein can determine if a patient has PD or does not have PD. In an embodiment, progression of PD can be determined (e.g., asymptomatic, early-stage, mid-stage or late-stage PD).

Treatment of Parkinson's Disease

In embodiments, the methods described herein include a step of treating a patient with PD. Treatment can prevent or ameliorate progression of the disease. Recent studies have shown that substantia nigra degeneration can be decelerated by treatment with iron binding compounds such as deferiprone. Further, compounds known to decrease PD risk including caffeine, niacin, nicotine and salbutamol which also have iron binding properties. Adequate function of antioxidative mechanisms in the vulnerable brain cells can be restored by acetylcysteine supplementation to normalize intracellular glutathione activity.

Treatment can also be aimed at managing signs/symptoms of PD. For example, medications can help a patient with walking, movement and tremor. These medications can increase or substitute for dopamine. Patients with Parkinson's disease have low brain dopamine concentrations. However, dopamine does not enter the brain. Medications can include, for example, carbidopa-levodopa. Levodopa is a natural chemical that passes into your brain and is converted to dopamine. Levodopa can be combined with carbidopa, which protects levodopa from early conversion to dopamine outside the brain. This prevents or lessens side effects such as nausea. Duopa is another medication, often given to patients with more advanced PD. Because Duopa is continually infused, blood levels of the two drugs remain constant.

Dopamine agonists are another option for treating patients with PD. Dopamine agonists can mimic dopamine effects of the brain. Dopamine agonists include pramipexole and rotigotine. Apomorphine is a short-acting injectable dopamine agonist that can be used for quick relief.

MAO B inhibitors can help prevent the breakdown of brain dopamine by inhibiting the brain enzyme monoamine oxidase B (MAO B) which metabolizes brain dopamine. These medications include selegiline, rasagiline and safinamide. Selegiline can be administered in combination with levodopa.

Catechol O-methyltransferase (COMT) inhibitors are another option. Entacapone and opicapone are the primary medications from this class. These medications can prolong the effect of levodopa therapy by blocking an enzyme that breaks down dopamine. Tolcapone is another COMT inhibitor that can be administered as an alternative.

Anticholinergics can be administered to help control the tremor associated with Parkinson's disease. Several anticholinergic medications are currently available, including benztropine or trihexyphenidyl. Amantadine can be administered to provide short-term relief of symptoms of mild, early-stage Parkinson's disease.

Adenosine receptor antagonists (A2A receptor antagonist) target areas in the brain that regulate the response to dopamine and allow more dopamine to be released. Istradefylline is an A2A antagonist drug that is currently available. Nuplazid can be administered to treat hallucinations and delusions that can occur with Parkinson's disease.

Non-pharmacological treatments for PD include surgical procedures (e.g., deep brain stimulation), MRI-guided focused ultrasound (MRgFUS), acupuncture, lifestyle changes, physical/occupational therapy, exercise, diet and herbal medications.

mRNA Biomarkers

Table 1 includes a list of mRNA biomarkers for detecting Parkinson's disease.

TABLE 1

| mRNA Biomarkers | | | |
|---|---|---|---|
| No. | Standard ID | Gene Symbol | Gene Name |
| 1 | NM_ 000376.1 | VDR | Vitamin D Receptor |
| 2 | 5730 | PTGDS | Prostaglandin D2 Synthase |
| 3 | 3738 | KCNA3 (Kv1.3) | Potassium Voltage-Gated Channel Subfamily A Member 3 |
| 4 | 10298 | PAK4, P21 (RAC1) | Activated Kinase 4 |
| 5 | 23135 | KDM6B (JMJD3), | Lysine Demethylase 6B |
| 6 | 335 | APOA1 | Apolipoprotein A1 |
| 7 | 54674 | LRRN3 | Leucine Rich Repeat Neuronal 3 |
| 8 | 9444 | QKI | QKI KH Domain Containing RNA Binding |
| 9 | 32 | ACACB (ACC2) | Acetyl-CoA Carboxylase Beta |
| 10 | U48734 | ACTN4 | Actinin Alpha 4 |
| 11 | 54434 | SSH1 | Slingshot Protein Phosphatase 1 |
| 12 | 115653 | KIR3DL3 | Killer Cell Immunoglobulin Like Receptor, Three Ig Domains and Long Cytoplasmic Tail 3 |
| 13 | 7710 | ZNF154 | Zinc Finger Protein 154 |
| 14 | 9086 | EIF1AY | Eukaryotic Translation Initiation Factor 1A |
| 15 | 55705 | IPO9 | Importin 9 |
| 16 | 11057 | ABHD2 | Abhydrolase Domain Containing 2, Acylglycerol Lipase2 |
| 17 | 29942 | PURG | Purine Rich Element Binding Protein G |
| 18 | 25854 | FAM149A | Family With Sequence Similarity 149 Member A |

Protein Biomarkers

Table 2 includes a list of protein biomarkers for detecting Parkinson's disease.

TABLE 2

| Protein Biomarkers | | | |
|---|---|---|---|
| No. | Standard ID | Gene Symbol | Gene Name |
| 1 | BC005378.1 | C4BPB | Complement Component 4 Binding Protein Beta |
| 2 | BC017305.1 | SIRT7 | Sirtuin 7 |
| 3 | BC012499.1 | SIRT1 | Sirtuin 1 |
| 4 | NM_012241.2 | SIRT5 | Sirtuin 5 |
| 5 | NM_006555.2 | YKT6 | YKT6 V-SNARE Homolog |
| 6 | BC001632.1 | NDUFV2 | NADH:Ubiquinone Oxidoreductase Core Subunit V2 |
| 7 | PHC0205 | IL20 | Interleukin 20 |
| 8 | NM_007360.1 | KLRK1 (NKG2D or CD314) | Killer Cell Lectin Like Receptor K1 |
| 9 | NM_002488.2 | NDUFA2 | NADH: Ubiquinone Oxidoreductase Subunit A2 |
| 10 | NM_004549.2 | NDUFC2 | NADH: Ubiquinone Oxidoreductase Subunit C2 |
| 11 | NM_003041.1 | SLC5A2 (SGLT2) | Solute Carrier Family 5 Member 2 |
| 12 | NM_021088.1 | ZNF2 | Zinc Finger Protein 2 |
| 13 | NM_022438.1 | MAL | Mal T Cell Differentiation Protein |
| 14 | PV4395 | MARK1 | Microtubule Affinity Regulating Kinase 1 |
| 15 | BC007022.1 | SAA1 | Serum Amyloid A1 |
| 16 | NM_002211.2 | ITGB1 | Integrin Subunit Beta 1 |
| 17 | BC014441.1 | NSUN4 | NOP2/Sun RNA Methyltransferase 4 |
| 18 | NM_016507.1 | CDK12 | Cyclin Dependent Kinase 12 |
| 19 | PHC1244 | CCL19 (ELC) | C-C Motif Chemokine Ligand 19 |
| 20 | NM_020750.1 | XPO5 | Exportin 5 |
| | BC013158.1 | APBB3 | Amyloid Beta Precursor Protein Binding Family B Member 3 |
| 22 | BC053557.1 | ZNF740 | Zinc Finger Protein 740 |
| 23 | BC006105.1 | C6orf134 (ATAT1) | Alpha Tubulin Acetyltransferase 1 |
| 24 | NM_145810.1 | CDCA7 | Cell Division Cycle Associated 7 |
| 25 | NM_152772.1 | TCP11L2 | T-Complex 11 Like 2 |
| 26 | BC030814.1 | IGKV1-5 | Immunoglobulin Kappa Variable 1-5 |
| 27 | BC006558.2 | HCFC2 | Host Cell Factor C2 |
| 28 | BC013966.2 | FAM64A (PIMREG) | PICALM Interacting Mitotic Regulator |
| 29 | NM_153339.1 | PUSL1 | Pseudouridine Synthase Like 1 |
| 30 | BC041174.1 | CYP2B7P1 | Cytochrome P450 Family 2 Subfamily B Member 7 |
| 31 | XM_378879.2 | LOC400763 | — |
| 32 | NM_003437.2 | ZNF136 | Zinc Finger Protein 136 |
| 33 | 55705 | IPO9 | Importin 9 |

Other methods for determining the level of the biomarker besides RT-PCR or another PCR-based method include proteomics techniques, as well as individualized genetic profiles. Individualized genetic profiles can be used to treat PD based on patient response at a molecular level. The specialized microarrays herein, (e.g., oligonucleotide microarrays or cDNA microarrays) can include one or more biomarkers having expression profiles that correlate with either sensitivity or resistance to one or more antibodies.

The one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be stored in a liquid or in a dry form, including, following lyophilization. If the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers are stored dry, the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be resuspended using water or a solution one of skill in the art would know would know would result in the stable resuspension of the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers.

Method of Detecting Parkinson's Disease Using Biomarkers

One or more of the biomarkers can be used in a method of diagnosing Parkinson's disease (PD) or determining a prognosis of a test subject with PD. In this manner, one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be used in a method of diagnosing PD or determining a prognosis of a test subject with PD. In this manner, at least one biomarker or a combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be used in a method of diagnosing PD or determining a prognosis of a test subject with PD.

In this manner, no more than one biomarker or a combination of no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be used in a method of diagnosing PD or determining a prognosis of a test subject with PD. In this manner, about one biomarker or a combination of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers can be used in a method of diagnosing PD or determining a prognosis of a test subject with PD.

In a first step, the expression levels of one or more mRNAs are measured in blood (or saliva) samples from subjects with PD. In an embodiment, the expression levels of one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers is used to generate a footprint or signature for subsequent diagnosis of patients. In an embodiment, the expression levels of at least one biomarker or a combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers is used to generate a footprint or signature for subsequent diagnosis of patients.

In an embodiment, the expression levels of no more than one biomarker or a combination of no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers is used to generate a footprint or signature for subsequent diagnosis of patients. In an embodiment, the expression levels of about one biomarker or a combination of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers is used to generate a footprint or signature for subsequent diagnosis of patients.

Next, expression levels of the same nucleic acids, including DNA and/or RNA and further are measured in blood (or saliva) samples from healthy subjects. This is used as a control. Thereafter, samples from healthy patients can be compared to identify mRNAs that have altered levels of expression in the plasma samples from the subjects with PD. A biomarker fingerprint or signature can be created from the mRNAs with altered levels of expression. This can be used for diagnosing or determining the prognosis of PD in the test subject by comparing of levels of mRNAs from the sample of the test subject. Conventional statistical analysis can be used to determine, for example, confidence levels. The same approach can be used to identify protein biomarkers, generate a biomarker footprint and diagnose or determine the prognosis of PD in a test subject by comparing of levels of protein biomarkers. In aspects, one or more mRNA biomarkers is used in combination with one or more protein biomarkers.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof.

Example 1

Discovery of mRNA Biomarkers

NIH Dataset I.D.: GSE99039—Whole Blood

A published data set was used to discover mRNA biomarkers that are predictive or indicative of the presence of Parkinson's disease (PD). The study included 233 control patients and 210 with early onset PD. The published study is cited as "Amar et al., A clinical profile of patients with Parkinson's disease and psychosis. Ann Indian Acad Neurol 2014; 17:187-92."

The assay platform (Affymetrix Human Genome U133 Plus2) utilized 54,675 probes. The study considered all variables using Liquid Biosciences' mathematical evolution modeling platform (see. e.g., U.S. Pat. No. 9,845,505). The approach is also detailed Applicant's previous published patent applications. A method of combining results from biomarkers is used to achieve a final categorical determination. Multiple biomarkers can be measured in a patient. The results can be compiled to produce a single categorical determination (see, e.g., U.S. Pat. No. 11,198,912).

The mRNA biomarkers and relevant descriptions are detailed in FIG. 1. In order to validate the markers, Applicants obtained three additional data sets of gene expression markers for PD patients. Sensitivity is the percentage of true positives (e.g., 90% sensitivity=90% of people who have the target disease will test positive). The specificity (also referred to as the True Negative Rate) is the proportion of people without the disease who had a negative result. The specificity of a test refers to how well a test identifies patients who do not have a disease. These data sets are discussed in the following examples:

Example 2

Validation of mRNA Biomarkers
NIH Dataset I.D.: GSE6613—Whole Blood

A published data set was used to validate the effectiveness of the biomarkers as predictive or indicative of the presence of PD. The study included 22 healthy controls, 33 other controls and 50 patients with early-onset PD. The published study is cited as "Scherzer et al., Molecular markers of early Parkinson's disease based on gene expression in blood. PNAS, Jan. 16, 2007, n. 3, 955-960."

As above, the study used Liquid Biosciences' mathematical evolution modeling platform (Affymetrix Human Genome U133A) with 22,277 probes. The validation process demonstrated that the markers had 96% sensitivity and 91 specificity.

Example 3

Validation of mRNA Biomarkers
NIH Dataset I.D.: GSE20291—Whole Blood

A second published data set was used to validate the effectiveness of the biomarkers as predictive or indicative of the presence of PD. The study included 10 healthy subjects and 15 subjects with late onset PD. The published study is cited as "Zhang et al., Genetics of Parkinson's disease and related disorders. J Med Genet. 2018 February; 55(2):73-80."

The same platform was used (Affymetrix Human Genome U133A) with 22,277 probes. The validation process demonstrated that the markers had 100% sensitivity and 100% specificity.

Example 4

Validation of mRNA Biomarkers
NIH Dataset I.D.: GSE20292—Whole Blood

A third published data set was used to validate the effectiveness of the biomarkers as predictive or indicative of the presence of PD. The study included 18 healthy control subjects and 11 with late onset PD. The published study is cited as "Middleton et al., Walking speed: the functional vital sign. J. Aging Phys. Act., 2015, 23, 314-322."

The same platform was used (Affymetrix Human Genome U133A) with 22,277 probes. The validation process demonstrated that the markers had 100% sensitivity and 100% specificity.

Example 5

Discovery of Protein Biomarkers
NIH Dataset I.D.: GSE62283—Serum

A fourth published data set was used to validate the effectiveness of the biomarkers as predictive or indicative of the presence of PD. The study included 156 healthy control subjects, 110 other control subjects, 103 subjects with early onset PD and 29 subjects with moderate PD. The published study is cited as Nagele et al., Diagnosis of Alzheimer's Disease Based on Disease-Specific Autoantibody Profiles in Human, 2011, Sera. PLoS ONE 6(8): e23112."

The protein biomarkers and relevant descriptions are detailed in FIG. 2. A different assay platform was used (Invitrogen ProtoArray v5.0). The validation process demonstrated that the markers had 94% sensitivity and 92% specificity.

Example 6

Validation of Protein Biomarkers
NIH Dataset I.D.: GSE29654—Serum

A fifth published data set was used to validate the effectiveness of the biomarkers as predictive or indicative of the presence of PD. The study included 80 healthy control subjects, 90 other control subjects, 174 subjects with PD. The published study is cited as Nagele et al.

The same platform was used (Invitrogen ProtoArray v5.0). The validation process demonstrated that the markers had 100% sensitivity and 98% specificity.

The results of the discovery and validation studies are summarized in Table 3 and Table 4 below. Not all of the original researchers published accuracy. In the studies in which it was published, the accuracy of the markers described herein was significantly higher than those published.

TABLE 3

Summary of Discovery/Validation Studies - mRNA

| Discovery GSE99039 (whole blood) | Validation GSE6613 (whole blood) | Validation GSE47860 (brain - putamen) | Validation GSE47860 (brain - subst. nigra) |
|---|---|---|---|
| 233 control | 22 healthy controls | 20 healthy controls | 18 healthy controls |
| 210 early PD | 33 other controls<br>50 early PD | 15 late PD | 11 late PD |
| Published: | Published: | Published: | Published: |
| Sensitivity — | Sensitivity 65% | Sensitivity — | Sensitivity — |
| Specificity — | Specificity 75% | Specificity — | Specificity — |
| Determined: | Determined: | Determined: | Determined: |
| Sensitivity 80% | Sensitivity 96% | Sensitivity 100% | Sensitivity 100% |
| Specificity 71% | Specificity 91% | Specificity 100% | Specificity 100% |

TABLE 4

Summary of Discovery/Validation Studies - protein

| Discovery GSE27567 (serum) | Validation GSE20266 (serum) |
|---|---|
| 156 healthy controls | 80 healthy controls |
| 110 other controls | |
| 103 early PD | 90 other controls |
| 29 moderate PD | 174 PD |
| Published: | Published: |
| Sensitivity 94% | Sensitivity 93% |
| Specificity 86% | Specificity 100% |
| Sensitivity 94% | Sensitivity 100% |
| Specificity 92% | Specificity 98% |

Example 7

Diagnostic Kit for Rapid Screening of Parkinson's Disease

The following working example is based on configurations described above. Embodiments of the invention can be compiled into a diagnostic kit for diagnosing PD. The kit can identify one or more target cells that have the biomarkers for PD in blood (whole blood, plasma or serum) from a test subject.

The kit can include a collection of nucleic acid molecules such that each nucleic acid molecule encodes a mRNA sequence. The nucleic acid molecules can be used to identify variations in expression levels of one or more mRNAs in a plasma sample from a test subject. The expression levels of the mRNAs can be used in a comparison/analysis of test samples with a fingerprint indicative of the presence of PD. The same approach can be used to identify protein biomarkers, generate a biomarker footprint and diagnose or determine the prognosis of PD in the test subject by comparing levels of protein biomarkers.

In certain embodiments, the present disclosure provides kits for diagnosing PD. The kits can include one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers disclosed herein. The skilled artisan will appreciate that the number of biomarkers may be varied without departing from the nature of the present disclosure, and thus other combinations of biomarkers are also encompassed by the present disclosure. The skilled artisan will know which one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers to use based on the symptoms of the patient suffering from PD.

In a specific embodiment, a kit includes the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers disclosed herein. In certain embodiments, the kit is for diagnosing PD. The kit can further optionally include instructions for use. The kit can further optionally include (e.g., comprise, consist essentially of, consist of) tubes, applicators, vials or other storage container with the above-mentioned biomarker and/or vials containing one or more of the biomarkers. In an embodiment, each biomarker is in its own tube, applicator, vial or storage container or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers are in a tube, applicator, vial or storage container.

The kits, regardless of type, will generally include one or more containers into which the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 biomarkers are placed and, preferably, suitably aliquoted. The components of the kits may be packaged either in aqueous media or in lyophilized form.

Example 8

Screening a Patient for Parkinson's Disease (Protein Biomarkers)

A female, age 64, presents to her doctor with a family history of PD but no noticeable signs or symptoms. The doctor draws a sample of blood and sends it to a lab to test for PD. The plasma is then tested to identify the presence of biomarkers associated with PD. The lab uses one or more of the following protein biomarkers in its test: C4BPB, SIRT7, SIRT1, SIRT5, YKT6, NDUFV2, IL20, KLRK1 (NKG2D or CD314), NDUFA2, NDUFC2, SLC5A2 (SGLT2), ZNF2, MAL, MARK1, SAA1, ITGB1, NSUN4, CDK12, CCL19 (ELC), XPO5, APBB3, ZNF740, C6orf134 (ATAT1), CDCA7, TCP11L2, IGKV1-5, HCFC2, FAM64A (PIMREG), PUSL1, CYP2B7P1, LOC400763, ZNF136 and IP09. Following the test, the lab determines that the one or more biomarkers used to test for PD are indicative of the presence of PD. Because of this result, the patient is contacted for further evaluation.

Upon a subsequent visit to the doctor, the patient is informed of the result. The doctor requests a specific single-photon emission computerized tomography (SPECT) scan (i.e., a dopamine transporter or "DAT" scan). The results of the scan and neurological examination confirm that the patient has early PD (i.e., stage I).

The PD does not affect the daily life of the patient. For this reason, the patient is periodically monitored for development of signs/symptoms of PD. The patient is administered an iron chelator (i.e., deferiprone at 25 mg/kg, orally, three times per day for a total of 75 mg/kg/day) to help prevent (or ameliorate) progression of PD. Treatment also includes lifestyle and dietary changes to prevent the disease from progressing.

Example 9

Screening a Patient for Parkinson's Disease (mRNA Biomarkers)

A male, age 70, presents to his doctor with gradual onset of mild problems with posture and balance. The doctor draws a sample of blood and sends it to a lab to test for PD. The plasma is tested to identify the presence of biomarkers associated with PD. The lab uses one or more of the following mRNA biomarkers in its test: VDR, PTGDS, KCNA3 (Kv1.3), PAK4, P21 (RAC1), KDM6B (JMJD3), APOA1, LRRN3, QKI, ACACB (ACC2), ACTN4, SSH1, KIR3DL3, ZNF154, EIF1AY, IPO9, ABHD2, PURG and FAM149A. Following the test, the lab determines that the one or more biomarkers are indicative of the presence of PD. Specifically, the test indicates that the patient has Stage I PD. Upon a subsequent visit to the doctor, the patient is informed of the result. The patient is examined and the doctor orders periodic biomarker testing to determine progression of the disease. The patient is administered therapeutics and subjected to physical therapy to help stop progression of the disease.

Specifically, efforts are made to slow progression of the disease (i.e., from Stage I to Stage II). The doctor recommends lifestyle changes, especially regular aerobic exercise. Physical therapy is also recommended with particular focus on balance and stretching. Pharmacological treatment includes selegiline administered in combination with levodopa. The patient is periodically evaluated for progression of signs/symptoms of PD.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Embodiments include a method of diagnosing Parkinson's disease (PD) or determining a prognosis of a subject with PD. The method can include steps of (a) measuring the expression level of at least one mRNA in a test sample from the subject, (b) receiving the expression level of the at least one mRNA in the test sample by a computer and (c) comparing the expression level of the at least one mRNA in the test sample to a level in a base sample for the same at least one mRNA, and (d) receiving a result comparing the expression levels of the at least one mRNA in the test sample measured in (a) and the base sample measured in (c), (e) diagnosing or determining the prognosis of Parkinson's disease based on altered expression of the at least one mRNA in the test sample as compared to the base sample, and (f) treating the subject based on the diagnoses or prognosis of Parkinson's disease. The mRNA can be one or more from those identified in Table 1.

The method can also include a step of measuring the expression level of at least one protein (i.e., from those listed in Table 2) in the test sample from the subject and comparing the expression level of the at least one protein in the test sample to a level in a base sample for the same at least one protein.

Embodiments include a method of diagnosing Parkinson's disease (PD) or determining a prognosis of a subject with PD. The method can include steps of (a) measuring the expression level of at least one protein in a test sample from the subject, (b) receiving the expression level of the at least one protein in the test sample by a computer and (c) comparing the expression level of the at least one protein in the test sample to a level in a base sample for the same at least one protein, and (d) receiving a result comparing the expression levels of the at least one protein in the test sample measured in (a) and the base sample measured in (c), (e) diagnosing or determining the prognosis of Parkinson's disease based on altered expression of the at least one mRNA in the test sample as compared to the base sample, and (f) treating the subject based on the diagnoses or prognosis of Parkinson's disease. The protein can be one or more from those identified in Table 2.

The method can also include a step of measuring the expression level of at least one mRNA (i.e., from those listed in Table 1) in the test sample from the subject and comparing the expression level of the at least one mRNA in the test sample to a level in a base sample for the same at least one mRNA.

Embodiments also include a method of diagnosing Parkinson's disease or determining a prognosis of a subject with early-onset or asymptomatic Parkinson's disease, that includes the steps of: (a) measuring an amount of one or more protein biomarkers in a blood or saliva sample from the subject, (i.e., from those listed in Table 2); (b) comparing the measured amount to a control and detecting an increase in the amount of the protein biomarker compared to the control; and (c) identifying the subject as having or having an increased probability of having Parkinson's disease and/or monitoring Parkinson's disease progression based on the detected increase in the level of protein biomarker.

Embodiments also include a method of diagnosing Parkinson's disease or determining a prognosis of a subject with early-onset or asymptomatic Parkinson's disease, that includes the steps of: (a) measuring an amount of one or more mRNA biomarkers in a blood or saliva sample from the subject, (i.e., from those listed in Table 1); (b) comparing the measured amount to a control and detecting an increase in the amount of the mRNA biomarker compared to the control; and (c) identifying the subject as having or having an increased probability of having Parkinson's disease and/or monitoring Parkinson's disease progression based on the detected increase in the level of mRNA biomarker.

In aspects, the methods can be used to create a biomarker fingerprint from the mRNAs/proteins with altered levels of expression to diagnosing or determine the prognosis of PD in a test subject.

Embodiments also include a diagnostic kit for diagnosing Parkinson's disease in a subject. The kit can include a plurality antibodies or antibody fragments, wherein each of the antibodies or antibody fragments has specificity to a protein biomarker, wherein the antibodies or antibody fragments identify variations in expression levels of respective protein biomarkers in a plasma or saliva sample from a test subject and wherein the expression levels of the protein biomarkers represent a protein expression fingerprint that is indicative for the presence of and Parkinson's disease.

Embodiments also include a method of evaluating a probability that a subject has Parkinson's disease, diagnosing Parkinson's disease and/or monitoring Parkinson's disease progression. The method can include steps of: (a) measuring an amount of one or more protein biomarkers in a sample from the subject (from those identified in Table 2); (b) comparing the measured amount to a control and detecting an increase in the amount of the protein biomarker compared to the control; and (c) identifying the subject as having or having an increased probability of having Parkinson's disease and/or monitoring Parkinson's disease progression based on the detected increase in the level of protein biomarker. The method can include also include a step of comparing mRNA biomarkers along with a treatment step.

Embodiments also include a method of evaluating a probability that a subject has Parkinson's disease, diagnosing Parkinson's disease and/or monitoring Parkinson's disease progression. The method can include steps of: (a) measuring an amount of one or more mRNA biomarkers in a sample from the subject (from those identified in Table 1); (b) comparing the measured amount to a control and detecting an increase in the amount of the mRNA biomarker compared to the control; and (c) identifying the subject as having or having an increased probability of having Parkinson's disease and/or monitoring Parkinson's disease progression based on the detected increase in the level of mRNA biomarker. The method can include a treatment step. The method can include also include a step of comparing protein biomarkers along with a treatment step.

What is claimed is:

1. A method of diagnosing or detecting Parkinson's disease in a subject, the method, comprising steps of:

a) obtaining a blood sample from the subject, b) measuring expression levels of KDM6B (JMJD3), SSH1, ZNF154 and FAM149A mRNAs in the blood sample, c) comparing the expression levels of KDM6B (JMJD3), SSH1, ZNF154 and FAM149A mRNAs to corresponding expression levels in a base sample obtained from one or more subjects that do not have Parkinson's disease, d) diagnosing or detecting Parkinson's disease in the subject when each of KDM6B (JMJD3), SSH1, ZNF154 and FAM149A is increased relative to the base sample, and e) after diagnosing or detecting Parkinson's disease, administering to the subject an effective amount of a dopamine agonist to treat Parkinson's disease.

2. The method of claim 1, wherein the Parkinson's disease is early-onset Parkinson's disease or asymptomatic Parkinson's disease.

3. The method of claim 1, further comprising a step of determining the severity of Parkinson's disease based on the presence of one or more symptoms of the disease.

4. The method of claim 3, wherein the severity of is one of Stage I, Stage II, Stage III, Stage IV and Stage V of Parkinson's disease.

5. The method of claim 1, further comprising a step of measuring the expression level of at least one additional mRNA selected from VDR, PTGDS, KCNA3 (Kv1.3), PAK4, P21 (RAC1), APOA1, LRRN3, QKI, ACACB (ACC2), ACTN4, SSH1, KIR3DL3, EIF1AY, IPO9, ABHD2, and PURG.

6. The method of claim 1, further comprising steps of measuring the expression level of at least one protein in the test sample from the subject and comparing the expression level of the at least one protein in the test sample to a level in a base sample for the same at least one protein.

7. The method of claim 6, wherein the at least one protein is selected from C4BPB, SIRT7, SIRT1, SIRT5, YKT6, NDUFV2, IL20, KLRK1 (NKG2D or CD314), NDUFA2, NDUFC2, SLC5A2 (SGLT2), ZNF2, MAL, MARK1, SAA1, ITGB1, NSUN4, CDK12, CCL19 (ELC), XPO5, APBB3, ZNF740, C6orf134 (ATAT1), CDCA7, TCP11L2, IGKV1-5, HCFC2, FAM64A (PIMREG), PUSL1, CYP2B7P1, LOC400763, ZNF136 and IPO9.

* * * * *